US012621637B2

(12) United States Patent
Park et al.

(10) Patent No.: US 12,621,637 B2
(45) Date of Patent: *May 5, 2026

(54) COMMUNICATION CONNECTION METHOD FOR CONTINUOUS BLOOD GLUCOSE MONITORING SYSTEM

(71) Applicant: I-SENS, INC., Seoul (KR)

(72) Inventors: Jeong Je Park, Seoul (KR); Bo Weol Kang, Seoul (KR); Ji Sun Park, Seoul (KR); Choong Beom You, Seoul (KR)

(73) Assignee: I-SENS, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/780,590

(22) Filed: Jul. 23, 2024

(65) Prior Publication Data

US 2024/0381061 A1     Nov. 14, 2024

Related U.S. Application Data

(63) Continuation of application No. 17/628,562, filed as application No. PCT/KR2020/003520 on Mar. 13, 2020, now Pat. No. 12,075,317.

(30) Foreign Application Priority Data

Aug. 9, 2019     (KR) ........................ 10-2019-0097272

(51) Int. Cl.
*H04W 4/38*          (2018.01)
*A61B 5/145*        (2006.01)
                    (Continued)

(52) U.S. Cl.
CPC ............. *H04W 4/38* (2018.02); *H04W 12/06* (2013.01); *H04W 76/14* (2018.02); *A61B 5/14532* (2013.01)

(58) Field of Classification Search
CPC ........... H04Q 2209/00; H04Q 2209/10; H04Q 2209/40; H04Q 2209/43; H04Q 2209/47;
                    (Continued)

(56) References Cited

U.S. PATENT DOCUMENTS 7,640,048 B2 * 12/2009 Dobbles .................. A61L 2/206
                                                        600/347
8,147,426 B2     4/2012 Neel et al.
                    (Continued)

FOREIGN PATENT DOCUMENTS

EP          3992977 A1     5/2022
JP      2003-521985 A     7/2003
                    (Continued)

*Primary Examiner* — Franklin D Balseca
(74) *Attorney, Agent, or Firm* — NKL Law; Jae Youn Kim

(57)          ABSTRACT

Provided relates to a communication connection method for a continuous glucose monitoring system which may comprise: a step in which, in order to connect communication between a communication terminal and a sensor transmitter attached to a human body so as to continuously monitor biometric information of the human body, the communication terminal receives information of the sensor transmitter from the sensor transmitter; a step of determining, on the basis of the received information, whether the sensor transmitter is a new sensor transmitter or an already used sensor transmitter; and a step in which, when the sensor transmitter is an already used transmitter, communication connection is controlled on the basis of use information of the already used sensor transmitter.

10 Claims, 9 Drawing Sheets

(51) Int. Cl.
    *H04W 12/06*     (2021.01)
    *H04W 76/14*     (2018.01)

(58) Field of Classification Search
    CPC ........... H04Q 2209/70; H04Q 2209/80; H04Q
               2209/82; H04Q 2209/84; H04Q 2209/86;
               H04Q 9/00; A61B 5/00; A61B 5/002;
               A61B 5/004; A61B 5/0015; A61B
               5/0022; A61B 5/0024; A61B 5/0026;
               A61B 5/14532; H04W 4/38; H04W
               76/14; H04W 12/06
    See application file for complete search history.

(56) References Cited

U.S. PATENT DOCUMENTS

| | | | |
|---|---|---|---|
| 9,654,847 B2 * | 5/2017 | Bergström | ............... H04Q 9/00 |
| 10,136,246 B2 * | 11/2018 | Yamada | ................ H04W 12/06 |
| 12,075,317 B2 * | 8/2024 | Park | ........................ H04W 4/38 |
| 2011/0221590 A1 | 9/2011 | Baker et al. | |
| 2014/0200426 A1 * | 7/2014 | Taub | .................. A61B 5/14532 |
| | | | 600/347 |
| 2016/0210099 A1 | 7/2016 | Hampapuram et al. | |

FOREIGN PATENT DOCUMENTS

| | | |
|---|---|---|
| JP | 2008-508029 A | 3/2008 |
| JP | 2017-538474 A | 12/2017 |
| KR | 10-2015-0129252 A | 11/2015 |
| KR | 10-2017-0044262 A | 4/2017 |
| KR | 10-2017-0056904 A | 5/2017 |
| KR | 10-2018-0044942 A | 5/2018 |

* cited by examiner

COMMUNICATION CONNECTION METHOD FOR CONTINUOUS BLOOD GLUCOSE MONITORING SYSTEM

CROSS REFERENCES TO RELATED APPLICATIONS

This application is a continuation of copending U.S. application Ser. No. 17/628,562, filed Jan. 20, 2022, which is incorporated herein by reference in its entirety, which in turn is a national stage application based on International Application No. PCT/KR2020/003520, filed Mar. 13, 2020, which claims priority from Korean Application No. 10-2019-0097272, filed Aug. 9, 2019.

TECHNICAL FIELD

The present disclosure is generally related to a communication connection method for a continuous blood glucose monitoring system, in more detail, a communication connection method for a continuous blood glucose monitoring system for communication connection between a sensor transmitter of the continuous blood glucose monitoring system continuously measuring blood glucose and a communication terminal receiving data measured by the sensor transmitter.

BACKGROUND

In order to manage diabetes, the continuous measurement of blood glucose is required, and therefore the demand for devices related to blood glucose measurement is steadily increasing. It has been confirmed through various studies that the occurrence of complications of diabetes is significantly reduced when diabetic patients strictly control blood glucose. Accordingly, it is very important for diabetics to regularly measure blood glucose in order to manage blood glucose.

In general, a finger prick method is mainly used for blood glucose management by diabetic patients and this type of blood sugar collection system helps the diabetic patients in managing their blood glucose, but it is difficult to accurately identify the blood glucose levels which are being frequently changed because it shows only the result at the time of the measurement. In addition, the finger prick type blood glucose device needs to collect blood several times from time to time even in a day, so diabetics have a burden on blood collection.

Diabetics patients generally experience hyperglycemia and hypoglycemia, and an emergency may occur in the hypoglycemic conditions. The patients may become unconscious or die if a hypoglycemic condition lasts for an extended period of time without the supply of sugar. Accordingly, rapid discovery of the hypoglycemic condition is critically important for diabetics. However, blood-collecting type glucose monitoring devices intermittently measuring glucose have limited ability to accurately measure blood glucose levels.

To overcome such a drawback, continuous glucose monitoring systems (CGMSs) inserted into the human body to measure a blood glucose level every few minutes have been developed, and therefore easily perform the management of diabetics and responses to an emergency situation.

A continuous blood glucose monitoring system comprises a sensor transmitter attached to human body of a user, extracting body fluid, and measuring blood glucose, and a communication terminal displaying a received blood glucose level. The sensor transmitter generates blood glucose information by measuring the blood glucose of the user for a certain period, for example, around fifteen (15) days, in a state that the sensor transmitter is inserted into the human body. The sensor transmitter periodically generates the blood glucose information, and the communication terminal periodically receives the blood glucose information and outputs the received blood glucose information so that the user can check the blood glucose information.

However, if the user deletes communication registration information of between the sensor transmitter and the communication terminal from the communication terminal or deletes a program or application installed at the communication terminal while using the continuous blood glucose monitoring system, the communication between the sensor transmitter and the communication terminal may be disconnected. In this case, the communication between the sensor transmitter and the communication terminal needs to be reconnected.

In this case, the sensor transmitter has a limited usable time period, and it is necessary to strictly limit the reuse of a sensor transmitter of which usable time period is expired, or to block the reuse of a sensor transmitter used by another user. Accordingly, when the communication connection between the sensor transmitter and the communication terminal is disconnected and then reconnected, it is necessary to check whether the sensor transmitter to be reconnected is a sensor transmitter of which usable time period is expired or a sensor transmitter used by another user. Accordingly, it is necessary to block the reuse of a sensor transmitter of which usable time period is expired or a sensor transmitter used by another user.

Additionally, if an existing user wants to continue to use a sensor transmitter of which usable time period is left, a novel communication connection method between the sensor transmitter and the communication terminal in which the communication connection between the sensor transmitter and the communication terminal is simplified and the convenience of the user is increased, and when using the sensor transmitter attached to the existing user, the existing user can use the sensor transmitter without stabilization process required to spend generally one (1) hour to three (3) hours is needed.

DETAILED DESCRIPTION OF DISCLOSURE

Technical Problem

To solve the problem of the conventional art, the purpose of the present disclosure may be for providing a communication connection method for a continuous blood glucose monitoring system checking whether a sensor transmitter to be communicationally connected to a communication terminal is a new product or a previously used product when connecting the communication between the sensor transmitter and the communication terminal, checking whether a usable time period is left when it is a previously used sensor transmitter, and selectively connecting the communication between the sensor transmitter and the communication terminal.

Another purpose of the present disclosure may be for providing a communication connection method for a continuous blood glucose monitoring system in which, when reconnecting communication between a sensor transmitter and a communication terminal, if the sensor transmitter is a previously used sensor transmitter, the communication terminal can receive blood glucose data measured by the sensor transmitter without a separate and additional stabilization process.

<div align="center">Solution to Problem</div>

According to an embodiment of the present disclosure, a communication connection method for a continuous blood glucose monitoring system may comprise: to connect communication between a sensor transmitter configured to be attachable to a body and continuously measure biometric information of the body and a communication terminal, receiving information of the sensor transmitter from the sensor transmitter; using the received information of the sensor transmitter, determining whether the sensor transmitter is a new sensor transmitter or a previously used sensor transmitter; and if the sensor transmitter is the previously used sensor transmitter, controlling communication connection based on use information of the previously used sensor transmitter.

The communication connection method may further comprise, if the sensor transmitter is the previously used sensor transmitter, determining whether a remaining usable time period of the previously used sensor transmitter is left, wherein the controlling of the communication connection comprises, if the remaining usable time period of the previously used sensor transmitter is left, controlling the communication connection.

The determining of whether the remaining usable time period of the previously used sensor transmitter is left comprises determining the determination of whether the remaining usable time period of the previously used sensor transmitter is left based on information about a time point in which the previously used sensor transmitter was attached and activated and information about a usable time period of the sensor transmitter.

The communication connection method may further comprise receiving, from the sever, information of the sensor transmitter which was previously transmitted from the communication terminal to the server, wherein the information of the sensor transmitter received from the server includes the information about the time point in which the previously used sensor transmitter was attached and activated and the information about the usable time period of the sensor transmitter The communication connection method may further comprise, if the sensor transmitter is the previously used sensor transmitter, determining whether a user of the previously used sensor transmitter is an existing user, wherein the controlling of the communication connection comprises, if the user of the previously used sensor transmitter is the existing user, controlling the communication connection.

The determining of whether the user of the previously used sensor transmitter is the existing user comprises determining of whether the user of the previously used sensor transmitter is the existing user based on the information received from the sensor transmitter.

The communication connection method may further comprise receiving, from the sensor transmitter, user information which was previously transmitted from the communication terminal to the sensor transmitter, wherein the determining of whether the user of the previously used sensor transmitter is the existing user comprises determining whether the user of the previously used sensor transmitter is the existing user by comparing the user information received from the sensor transmitter with user information verified by the communication terminal and determining whether the user information received from the sensor transmitter is identical to the user information verified by the communication terminal.

The communication connection method may further comprise receiving, from the server, information of the sensor transmitter which was previously transmitted from the communication terminal to the server, wherein the determining of whether the sensor transmitter is the previously used sensor transmitter comprises determining whether the sensor transmitter is the previously used sensor transmitter by comparing the information of the sensor transmitter received from the server with the information received from the sensor transmitter and determining whether the information of the sensor transmitter received from the server is identical to the information received from the sensor transmitter.

The communication connection method may further comprise, if the sensor transmitter is the previously used sensor transmitter, checking whether the previously used sensor transmitter continues to be used, wherein the checking of whether the previously used sensor transmitter continues to be used comprises checking whether the previously used sensor transmitter continues to be used based on information inputted to the communication terminal by the user.

The communication connection method may further comprise, if the communication connection with the previously used sensor transmitter is performed, receiving and storing, by the communication terminal, biometric information data measured by the sensor transmitter, and outputting the received biometric information data on the communication terminal, wherein the communication terminal stores and outputs biometric information data previously transmitted by the sensor transmitter and the biometric information data received after the communication connection with the previously used sensor transmitter is performed.

<div align="center">Advantageous Effects of Invention</div>

According to the present disclosure, there is an advantageous technical effect in that, when communication connection between a sensor transmitter inserted into a human body and a communication terminal receiving blood glucose data from the sensor transmitter is disconnected and then the connection between the previous sensor transmitter and the communication terminal is reconnected, the communication can be connected quickly.

Additionally, there is an advantageous technical effect of preventing a case in which a sensor transmitter being used by a user is mistakenly connected to a communication terminal being used by another user.

Furthermore, there is an advantageous technical effect in that, even though a user uses a new communication terminal, a user can keep continuously using a sensor transmitter which the user is using, and when the sensor transmitter is a sensor transmitter which the user is using, the user can immediately use that sensor transmitter without an additional stabilization period.

In addition, there is an advantageous technical effect in that, after a usable time period of a sensor transmitter used by a user is expired, the reuse of that sensor transmitter can be prevented in advance, and therefore the reliability of a product can be increased.

<div align="center">BRIEF DESCRIPTION OF THE DRAWINGS</div>

DESCRIPTION OF EMBODIMENTS OF DISCLOSURE

With reference to enclosed drawings, preferred embodiments of the present disclosure are described in detail.

The technical terms used in the present disclosure are only for the purpose of describing exemplary embodiments, and they are not intended to limit the present invention. Also, unless otherwise defined, all technical terms used herein should be construed as having the same meaning as commonly understood by those skilled in the art, and should not be interpreted as being excessively inclusive or excessively restrictive. In addition, when a technical term used herein is an erroneous technical term that does not accurately represent the idea of the present invention, it should be understood as replacing the term by a technical term which can be properly understood by those skilled in the art.

Further, singular expressions used in the present specification include plural expressions unless they have definitely opposite meanings. In the present application, it shall not be construed that terms, such as "including" or "comprising", various constituent elements or steps described in the specification need to be all essentially included, and it shall be construed that some constituent elements or steps among the various constituent elements or steps may be omitted, or additional constituent elements or steps may be further included.

Also, it should be noted that the accompanying drawings are merely illustrated to easily explain the spirit of the invention, and therefore, they should not be construed to limit the spirit of the invention by the accompanying drawings.

Hereinafter, with reference to the enclosed drawings, a method for stabilizing a continuous blood glucose monitoring system according to an embodiment of the present disclosure is described in detail.

Figure 1:
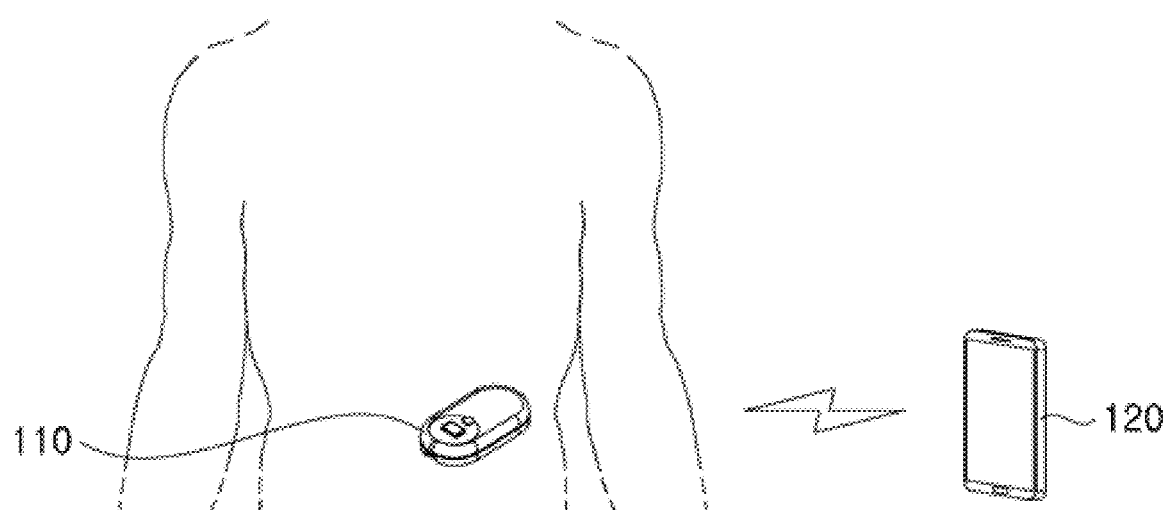
FIG. 1 is a schematic diagram for illustrating a continuous blood glucose measurement system according to an embodiment of the present disclosure.

FIG. 1 is a schematic diagram for illustrating a continuous blood glucose measurement system according to an embodiment of the present disclosure.

Referring to FIG. 1, the continuous blood glucose measurement system according to an embodiment of the present disclosure comprises a sensor transmitter (110) and a communication terminal (120).

The sensor transmitter (110) is attachable to human body and, when the sensor transmitter (110) is attached to the human body, an end portion of a sensor of the sensor transmitter (110) is inserted into skin to periodically extract body fluid of the human body and measure blood glucose.

The communication terminal (120) is a terminal configured to receive blood glucose information from the sensor transmitter (110) and output or display the received blood glucose information to a user, and for example, the communication terminal (120) may be a portable terminal (such as smartphone, tablet PC, or notebook and so on) configured to communicate with the sensor transmitter (110). However, the communication terminal (120) is not limited thereto, and may be any type of a terminal which has a communication function and program or application can be installed to.

The sensor transmitter (110) transmits the blood glucose information in response to request of the communication terminal (120) or at predetermined times periodically, and for data communication between the sensor transmitter (110) and the communication terminal (120), the sensor transmitter (110) and the communication terminal (120) are communicationally connected to each other over a wire by an USB cable and so on or communicationally connected in an wireless communication means such as infrared communication, NFC communication, Bluetooth, etc.

Figure 2:
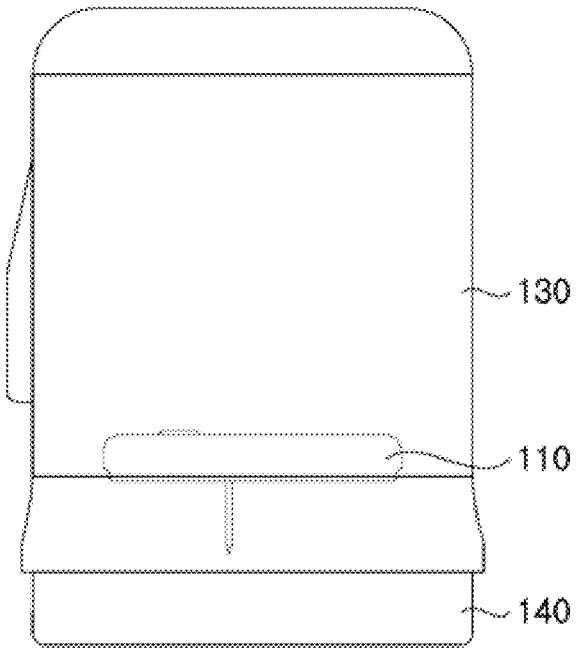
FIG. 2 is a figure illustrating an applicator for attaching a sensor transmitter to a part of a human body according to an embodiment of the present disclosure.
Figure 3:
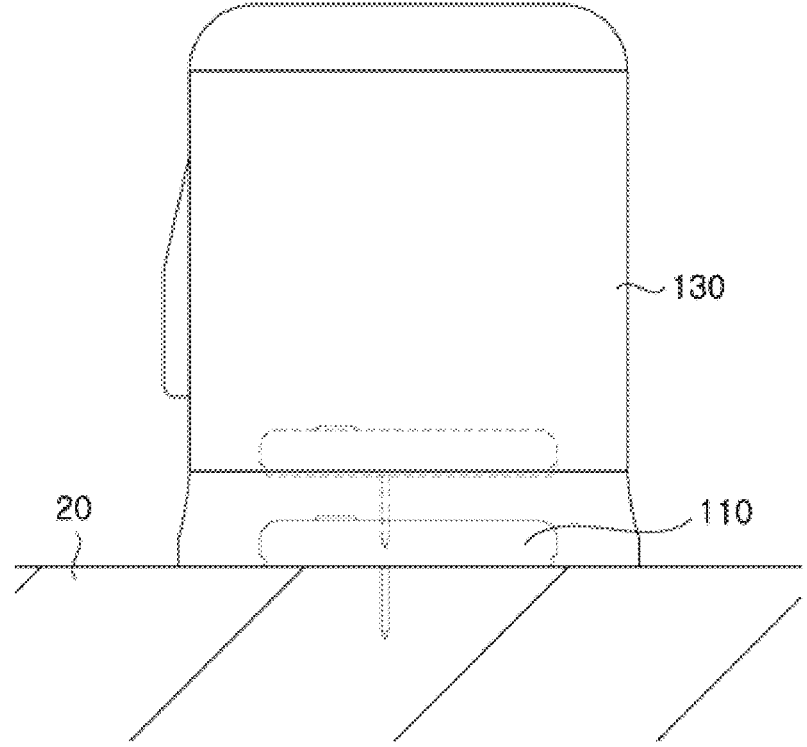
FIGS. 3 and 4 are figures for illustrating a process of attaching a sensor transmitter to a human body using an applicator according to an embodiment of the present disclosure.
Figure 4:
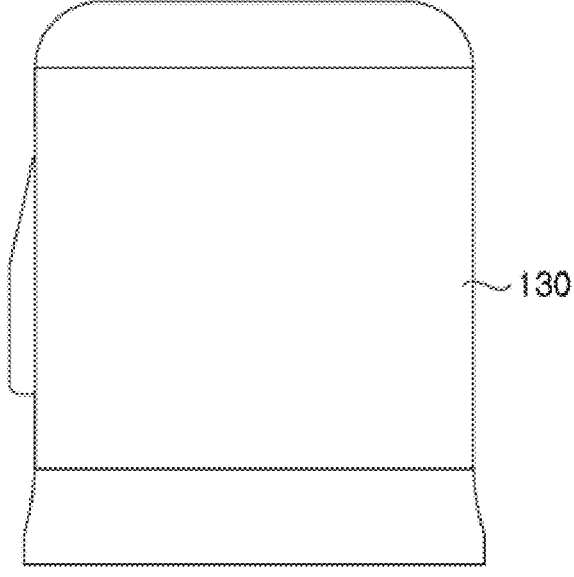
Figure 4:
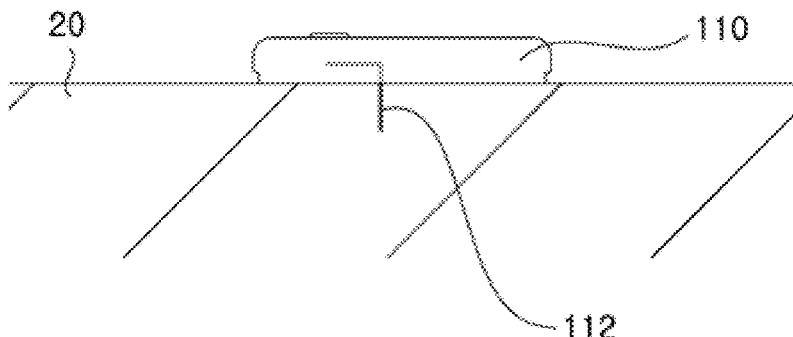

The sensor transmitter (110) is attached to a part of the human body by an applicator, FIG. 2 is a figure illustrating an applicator for attaching a sensor transmitter to a part of a human body according to an embodiment of the present disclosure, and FIGS. 3 and 4 are figures for illustrating a process of attaching a sensor transmitter to a human body using an applicator according to an embodiment of the present disclosure.

Firstly, an application (130) is now described by referring to FIG. 2, the sensor transmitter (110) is mounted in the applicator (130), and the applicator (130) can be operated so that the sensor transmitter (110) can be outwardly discharged to the outside of the applicator (130) by the manipulation of the user and then be attached to a specific portion of the human body of the user. The applicator (130) is formed to have a shape that one side of the applicator (130) is open, and the sensor transmitter (110) is installed to the applicator (130) through the open side of the applicator (130).

When the sensor transmitter (110) is attached to a part of the human body using the applicator (130), for inserting an end portion of the sensor included in the sensor transmitter (110) to skin, the applicator (130) comprises a needle (not shown) formed to cover the end portion of the sensor therein, a first elastic means (not shown) pushing the needle and the end portion of the sensor together towards the skin, and a second elastic means (not shown) configured to retract the needle only. The compressed state of the first elastic means (not shown) arranged to be compressed inside the applicator (130) by the configuration of the applicator (130) can be released, thereby inserting the needle and the end portion of the sensor simultaneously to the skin, and when the end portion of the sensor is inserted to the skin, the compressed state of the second elastic means (not shown) is released, thereby extracting the needle only. By the applicator (130), the user can safely and easily attach the sensor transmitter (110) to the skin.

A process of attaching the sensor transmitter (110) to the human body will be described in detail with reference to FIGS. 3 and 4, in a state that a protection cap (140) is separated or removed, an open side of the applicator (130) is closely placed on a specific part of skin (20) of the human body. When the applicator (130) is operated in a state that the applicator (130) is closely placed on the skin (20) of the human body, the sensor transmitter (110) is outwardly discharged from the applicator (130) and then attached to the skin (20). Here, an end portion of the sensor (112) is arranged to be exposed from the sensor transmitter (110) at a lower portion of the sensor transmitter (110), and a part of the end portion of the sensor (112) is inserted into the skin (20) by a needle installed at the applicator (130). Accordingly, the sensor transmitter (110) can be attached to the sensor (20) in a state that an end portion of the sensor (112) is inserted to the skin (20).

In the embodiment of the present disclosure, an adhesive tape is provided at a surface of the sensor transmitter (110) contacting the human body so that the sensor transmitter (110) can be attached to the skin (20). Accordingly, if the applicator (130) is moved away from the skin (20) of the human body, the sensor transmitter (110) is fixedly attached to the skin (20) of the human body by the adhesive tape.

After that, if the power is supplied to the sensor transmitter (110), the sensor transmitter (110) is communicationally connected with the applicator (130), and the sensor transmitter (110) transmits the measured blood glucose information to the communication terminal.

The sensor transmitter (110) can measure not only the blood glucose information but also various biometric information, and hereinafter blood glucose information is illustrated as one of examples of biometric information.

Figure 5:
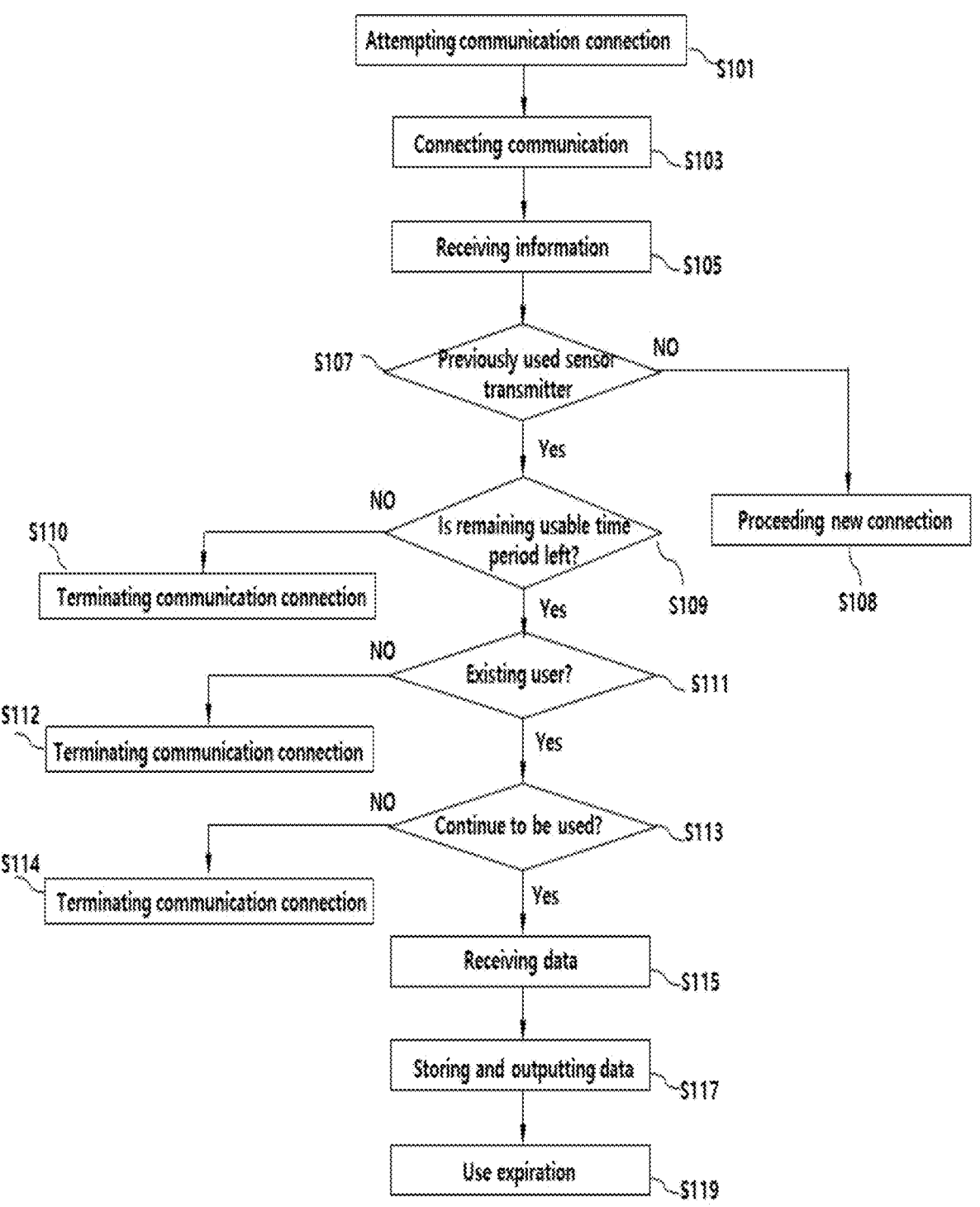
FIG. 5 is a flowchart for illustrating a method for communication connection of a continuous blood glucose monitoring system according to an embodiment of the present disclosure.

FIG. 5 is a flowchart for illustrating a method for communication connection of a continuous blood glucose monitoring system according to an embodiment of the present disclosure.

Referring to FIG. 5, the communication terminal (120) attempts to connect communication for connecting the communication with the sensor transmitter (110) (S101).

In the present disclosure, the communication terminal (120) is communicationally connected with the sensor transmitter (110) through a Bluetooth communication standard. Accordingly, the operation of attempting the communication connection can be an operation of pairing with the sensor transmitter (110) performed by the communication terminal (120).

As described above, if the communication terminal (120) attempts the communication connection to the sensor transmitter (110), the communication terminal (120) and the sensor transmitter (110) are communicationally connected to each other (S103).

At that time, by connecting the communication of the communication terminal (120) and the sensor transmitter (110), the transmission of various types of information between the communication terminal (120) and the sensor transmitter (110) can be performed. However, according to the present application, at step S103, even though the communication is connected, blood glucose information data measured by the sensor transmitter (110) may not be transmitted.

Like this, if the communication connection of the communication terminal (120) and the sensor transmitter (110) is completed, the communication terminal (120) receives information regarding the sensor transmitter (110) from the sensor transmitter (110) (S105).

The information received from the sensor transmitter (110) may be identification or unique information of the sensor transmitter (110), such as an identifier and a serial number of the sensor transmitter (110), and information on an activation time point of the sensor transmitter (110) and a usable time period of the sensor transmitter (110).

The communication terminal (120) determines whether the sensor transmitter (110) communicationally connected with the communication terminal (120) is a previously used sensor transmitter (110) or not based on the information received from the sensor transmitter (110) (S107).

The communication terminal (120) determines whether the sensor transmitter (110) communicationally connected with the communication terminal (120) is a previously used sensor transmitter (110) or not based on whether the communication terminal (120) has a record that the sensor transmitter (110) communicationally connected with the communication terminal (120) has been communicationally connected with the communication terminal (120) before. Because the identification or unique information, such as an identifier and serial number, are received from the sensor transmitter (110) and stored at the communication terminal (120) if the communication terminal (120) is communicationally connected with the sensor transmitter (110), the communication terminal (120) is in a state that the identification or unique information of the sensor transmitter (110) previously connected is stored at the communication terminal (120).

Accordingly, by comparing the identification or unique information of the sensor transmitter (110), such as an identifier and serial number, received at step S105 with the identification or unique information of the sensor transmitter (110), such as an identifier and serial number, previously stored at the communication terminal (120), the communication terminal (120) can determine whether the sensor transmitter (110) communicationally connected to the communication terminal (120) is a sensor transmitter which was previously used by being communicationally communicated before.

If the communication terminal (120) determines that the sensor transmitter (110) is a sensor transmitter which has not been previously used before, the communication terminal (120) proceeds the operation of new connection with that sensor transmitter (110) (S108).

When performing new communication connection of the communication terminal (120) and a new sensor transmitter (110), the communication terminal (120) receives from the new sensor transmitter (110) and stores identification or unit information, such as an identifier and serial number, information on an activation time point of the new sensor transmitter (110) and information on a usable time period of the new sensor transmitter (110). And, the communication terminal (120) receives blood glucose information data measured by the new sensor transmitter (110) from the new sensor transmitter (110).

However, if the communication terminal (120) determines that the sensor transmitter (110) is a sensor transmitter which was previously used before, the communication terminal (120) determines whether a remaining usable time period of the sensor transmitter (110) is left (S109).

The determination regarding whether the remaining usable time period of the sensor transmitter (110) is left can be determined by calculating an actual use time period of the sensor transmitter (110) using an activation time point of the sensor transmitter (110) received from the sensor transmitter (110) at step S105 and a current time point, and comparing the calculated actual use time period of the sensor transmitter (110) with the usable time period of the sensor transmitter (110) received from the sensor transmitter (110). Accordingly, if the calculated actual use time period is smaller than the usable time period received from the sensor transmitter (110), the communication terminal (120) determines that the remaining usable time period of the sensor transmitter (110) is still left.

And, if the calculated actual use time period is equal to or greater than the usable time period received from the sensor transmitter (110), the communication terminal (120) determines that no remaining usable time period of the sensor transmitter (110) is left. If the remaining usable time period of the sensor transmitter (110) is not left, the communication terminal (120) terminates the communication connection with the sensor transmitter (110) (S110).

By terminating the communication connection between the communication terminal (120) and the sensor transmitter (110) if no remaining usable time period of the sensor transmitter (110) is left, the reuse of the sensor transmitter (110) having no remaining usable time period can be prevented.

Meanwhile, if the remaining usable time period is still left, the communication terminal (120) determines whether a user of the sensor transmitter (110) communicationally connected with the communication terminal (120) is an existing user (S111).

As described above, if the sensor transmitter (110) is communicationally connected with the communication terminal (120), the communication terminal (120) stores the identification or unique information of the communicationally connected sensor transmitter (110). Accordingly, by comparing the identification or unique information of the sensor transmitter (110), such as an identifier and a serial number of the sensor transmitter (110), received at step S105 with the identification or unique information of the sensor transmitter (110), such as an identifier and a serial number of the sensor transmitter (110), stored at the communication terminal (120), the communication terminal (120) determines that the user of the communicationally connected sensor transmitter (110) is an existing user when the identification or unique information identical to the received identification or unique information of the sensor transmitter (110) was previously stored and registered at the communication terminal (120).

If the communication terminal (120) determines that the user of the sensor transmitter (110) is not an existing user, the communication terminal (120) terminates the communication connection with the sensor transmitter (110) (S112). By terminating, by the communication terminal (120), the communication connection with the sensor transmitter (110), a problematic case in which blood glucose information data of different users is mixed together can be prevented.

And, if the communication terminal (120) determines that the user of the sensor transmitter (110) is the same as a user who has been using a previous sensor transmitter, the communication terminal (120) checks whether the sensor transmitter (110) will continue to be used (S113).

The communication terminal (120) can output or display, on the communication terminal (120), an alarm message for checking whether the user wishes to continue to use the sensor transmitter (110), and in response to the alarm message, the user can input a user commend for selection regarding whether the sensor transmitter (110) continues to be used to the communication terminal (120).

If based on the inputted user command it is confirmed that the user does not continue to use that sensor transmitter (110), the communication terminal (120) terminates the communication connection with that sensor transmitter (110) (S114).

Meanwhile, if based on the inputted user command it is confirmed that the user continues to use that sensor transmitter (110), the communication terminal (120) receives blood glucose information data from the sensor transmitter (110) (S115).

At that time, the blood glucose information data to be transmitted from the sensor transmitter (110) to the communication terminal (120) can be transmitted at predetermined time intervals. Additionally, blood glucose information data which has not been transmitted from the sensor transmitter (110) to the communication terminal (120) for a time period of disconnection of the communication between the communication terminal (120) and the sensor transmitter (110) can be transmitted at once.

If the communication terminal (120) receives the blood glucose information from the sensor transmitter (110), the received blood glucose information data is stored to the communication terminal (120) and is displayed on the communication terminal (120) (S117).

When the communication terminal (120) outputs or displays the blood glucose information data received from the previously used sensor transmitter (110), the communication terminal (120) can output or display the blood glucose information data previously stored to the communication terminal (120) together. When the received blood glucose information data is a data continued from the blood glucose information data previously stored at the communication terminal (120) in time order, the communication terminal (120) continuously displays the previously stored blood glucose information data and the received blood glucose information data together in a time sequence. However, if there is a time gap between the received blood glucose information data and the blood glucose information data previously stored at the communication terminal (120), the time gap can be displayed on the communication terminal (120), or the communication terminal (120) can request the sensor transmitter (110) to transmit blood glucose information data corresponding to the time gap and display the blood glucose information data without the time gap.

After the communication terminal (120) and the sensor transmitter (110) are reconnected, the communication terminal (120) stores and displays the blood glucose information data received from the sensor transmitter (110) until the time point of the expiration of the usable time period of the sensor transmitter (110). And, if the usable time period of the sensor transmitter (110) expires (S119), the communication terminal (120) terminates the communication with the sensor transmitter (110).

Figure 6:
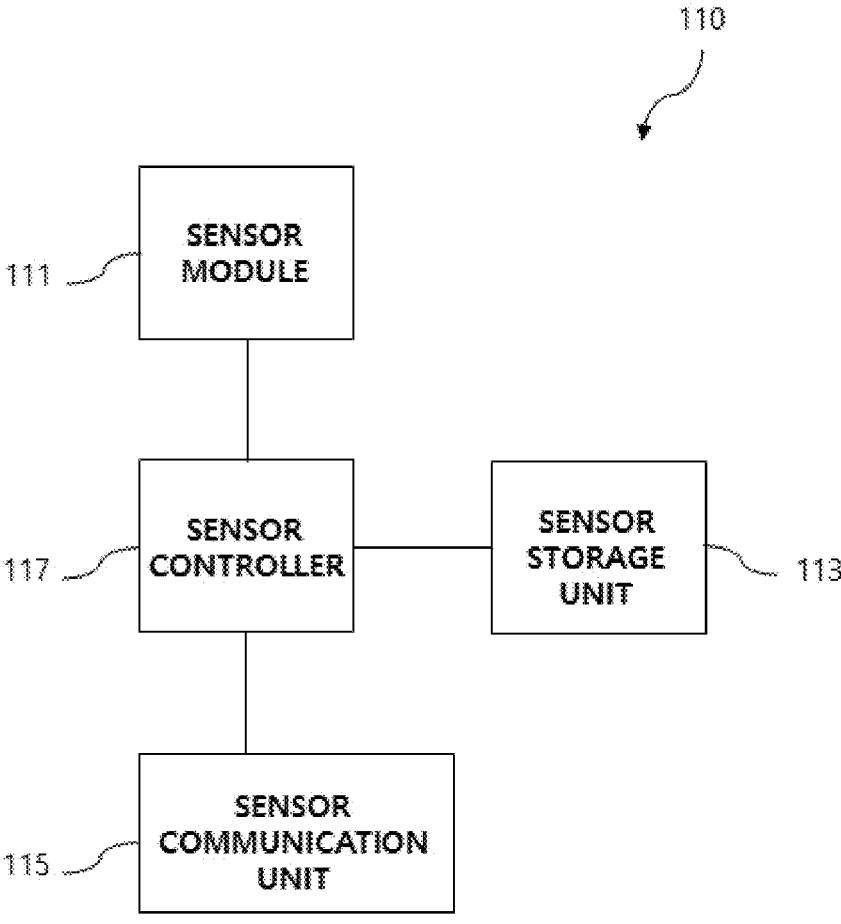
FIG. 6 is a block diagram for illustrating a sensor transmitter of a continuous blood glucose monitoring system according to an embodiment of the present disclosure.

FIG. 6 is a block diagram for illustrating a sensor transmitter of a continuous blood glucose monitoring system according to an embodiment of the present disclosure.

Referring to FIG. 6, a sensor module (111) comprises a sensor, and a part of the sensor can be inserted into a human body to measure blood glucose information. The sensor comprises a distal portion, a body, and a proximal portion, and the blood glucose information measured by the distal portion can be transferred to a sensor communication unit (115) through a tracer of the body and an electronic pad arranged to the proximal portion.

The usable time period of the sensor module (111) can be limited to a certain time period, such as about one (1) week, fifteen (15) days, or thirty (30) days. When the usable time period of the sensor module (111) is expired, the blood glucose information is not measured or monitored anymore even though a state that the sensor is inserted to the human body is maintained.

The sensor controller (117) receives the blood glucose information measured by the sensor module (111), and stores the received blood glucose information to a sensor storage unit (113). At that time, the blood glucose information measured by the sensor module (111) is an analog signal, and this analog signal can be transformed into a digital signal by the sensor controller (117).

If the communication terminal (120) and the sensor transmitter (110) are communicationally connected to each other, the sensor controller (117) controls a sensor communication unit to transmit, to the communication terminal (120), identification or unique information of the sensor transmitter (110), such as an identifier or a serial number of the sensor transmitter (110), information on a time point in which the sensor transmitter (110) is activated, and information on a usable time period of the sensor transmitter (110).

Figure 7:
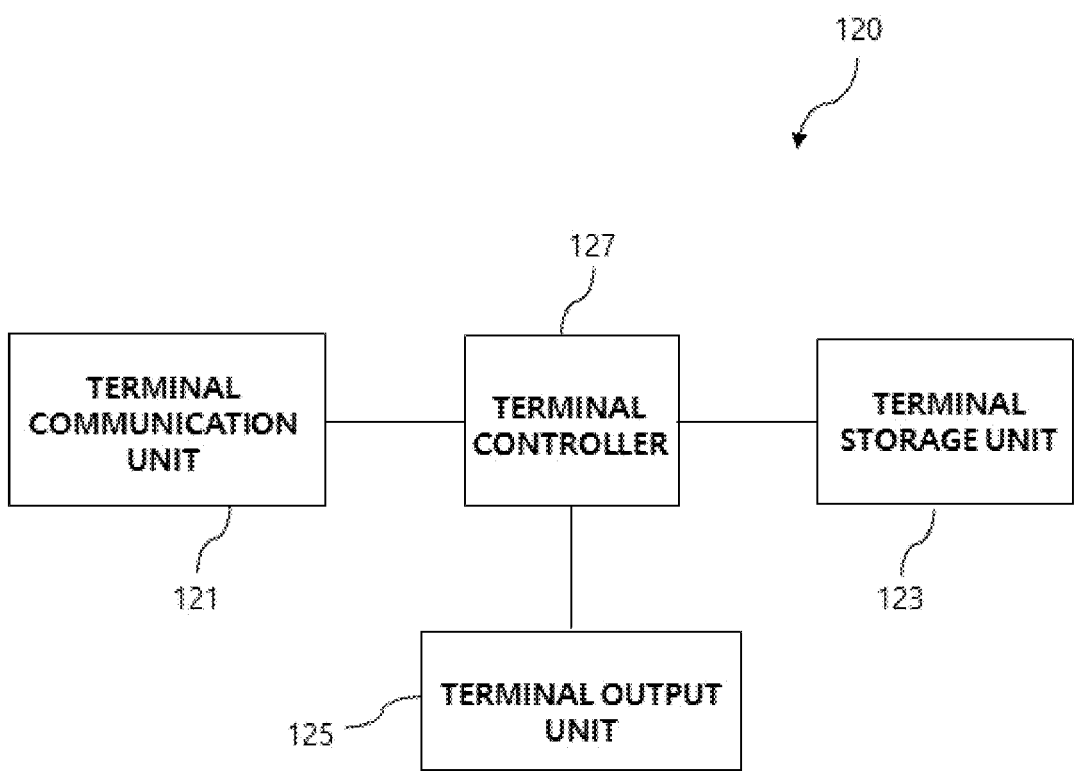
FIG. 7 is a block diagram for illustrating a communication terminal of a continuous blood glucose monitoring system according to an embodiment of the present disclosure.

FIG. 7 is a block diagram for illustrating a communication terminal of a continuous blood glucose monitoring system according to an embodiment of the present disclosure.

Referring to FIG. 7, the terminal controller (127) connects the communication with the sensor transmitter (110), receives various types of information associated with or related to the sensor transmitter (110) from the communicationally connected sensor transmitter (110), and perform determination of whether to use the communicationally connected sensor transmitter (110) or not.

Accordingly, the terminal controller (127) determines whether the communicationally connected sensor transmitter (110) is a sensor transmitter which was previously used, or whether a remaining usable time period is left, or whether a user who uses the sensor transmitter (110) is an existing user. And, the terminal controller (127) requests a user to confirm whether to continue to use the communicationally connected sensor transmitter (110).

The terminal controller (127) decides whether to use the communicationally connected sensor transmitter (110) using various conditions described above, controls the terminal communication unit (121) to receive blood glucose information data satisfying one or more use conditions from the sensor transmitter (110), controls to store the received blood glucose information data to the terminal storage unit (123). Additionally, the terminal controller (127) controls to output or display the blood glucose information data on a terminal output/display unit (125) so that the user can check the received blood glucose information data.

The terminal controller's (127) operation of determining whether to use the communicationally connected sensor transmitter (110) will be described in further detail. The terminal controller (127) compares identification or unique information, such as an identifier and a serial number, received from the sensor transmitter (110) with identification or unique information, such as an identifier and a serial number, previously stored at the terminal storage unit (123). If the compared information matches, or is not identical to, each other, the terminal controller (127) determines that the communicationally connected sensor transmitter (110) is the previously used sensor transmitter (110).

If the compared information does not match each other, the terminal controller (127) determines that the communicationally connected sensor transmitter (110) is a new sensor transmitter, and performs an operation of communication connection with the new sensor transmitter.

When the terminal controller (127) determines that the communicationally connected sensor transmitter (110) is a previously used sensor transmitter, the terminal controller (127) determines whether the remaining usable time period of the sensor transmitter (110) is left at current time using information on an activation time point of the sensor transmitter (110) and an usable time period of the sensor transmitter (110), received from the sensor transmitter (110).

When the remaining usable time period of the sensor transmitter (110) is left, the terminal controller (127) maintains the communication connection of the sensor transmitter (110). However, if the remaining usable time period of the sensor transmitter (110) is not left, the terminal controller (127) terminates the communication connection with the sensor transmitter (110) to prevent the reuse of the sensor transmitter (110) of which remaining usable time period is expired.

Meanwhile, if the communicationally connected sensor transmitter (110) is a previously used sensor transmitter and the remaining usable time period of the communicationally connected sensor transmitter (110) is still left, the terminal controller (127) compares identification or unique information, such as an identifier and a serial number, received from the sensor transmitter (110) with identification or unique information, such as an identifier and a serial number, stored at the terminal storage unit (123). When the compared information matches, or is identical to, each other, the terminal controller (127) determines that a user of the communicationally connected sensor transmitter (110) is the same user as an existing user.

Here, a verification process with respect to a user can be performed through a log-in operation by executing a program or application installed to the communication terminal (120), and, through this process, the terminal controller (127) can acquire information about the user. The terminal controller (127) controls to store the acquired user information and the identification information of the sensor transmitter (110) which the user uses.

Accordingly, the terminal controller (127) can check whether the user of the sensor transmitter (110) is an existing user who previously used the sensor transmitter (110) by comparing the information received from the sensor transmitter (110) and the information stored at the terminal storage unit (123).

When the user of the sensor transmitter (110) is the same as an existing user of the communicationally connected sensor transmitter, the terminal controller (127) maintains the communication connection with the sensor transmitter (110). However, if the user of the communicationally connected sensor transmitter (110) is different from the existing user, the terminal controller (127) terminates the communication connection with the sensor transmitter (110).

Meanwhile, if the communicationally connected sensor transmitter (110) is a previously used sensor transmitter, the remaining usable time period of the communicationally connected sensor transmitter (110) is left, and the user of the communicationally connected sensor transmitter (110) is the same as an existing user, the terminal controller (127) controls to output a display regarding a question of continuation use or not on the terminal output unit to check whether to continue to use the communicationally connected sensor transmitter (110). When a user command to continue to use the sensor transmitter (110) is inputted, the terminal controller (127) maintains the communication connection with the sensor transmitter (110), but, when a user command not to continue to use the sensor transmitter (110) anymore is inputted, the terminal controller (127) terminates the communication connection with the sensor transmitter (110).

Figure 8:
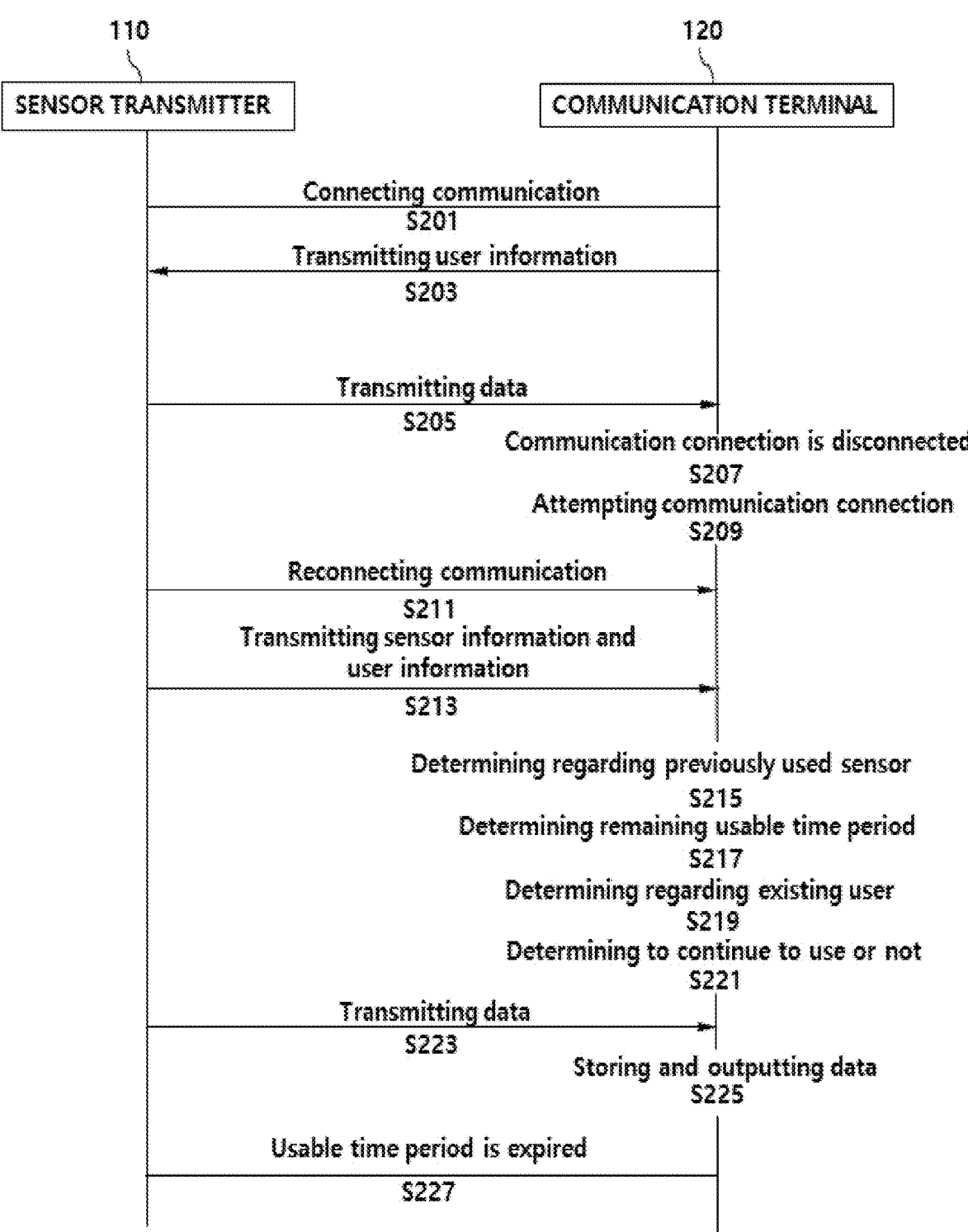
FIG. 8 is a flowchart for illustrating a method of communication connection of a continuous blood glucose monitoring system according to another embodiment of the present disclosure.

FIG. 8 is a flowchart for illustrating a method of communication connection of a continuous blood glucose monitoring system according to another embodiment of the present disclosure.

A communication connection method of a continuous blood glucose monitoring system (100) according to another embodiment of the present disclosure will be described with reference to FIG. 8. When describing the present embodiment, the descriptions of the embodiments described above which can be applied to, or be the same as or similar to, the present embodiment will be omitted.

A case of reconnecting the communication of the communication terminal (120) and the sensor transmitter (110) according to the present disclosure when the communication connection between the communication terminal (120) and the sensor transmitter (110) is disconnected will be described.

If it is a case that the communication connection between the communication terminal (120) and the sensor transmitter (110) is simply disconnected, the information related to the sensor transmitter (110) is still stored at the communication terminal (120), and therefore, as previously described with respect to the embodiments above, the communication between the communication terminal (120) and the sensor transmitter (110) can be reconnected.

However, in a case that the communication connection between the communication terminal (120) and the sensor transmitter (110) is disconnected due to the uninstall or removal of the program or application from the communication terminal (120), information related to or associated with the sensor transmitter (110) or the previously received blood glucose information data may be deleted together. Or, the user can use a new communication terminal, and therefore the communication connection between the previously used communication terminal (120) and the sensor transmitter (110) may be disconnected. At that case, the information related to or associated with the previous sensor transmitter (110) or the blood glucose information data transmitted from the previous sensor transmitter (110) may not be stored at new communication terminal (120).

Accordingly, in the present embodiment, a case of reconnecting the communication between the communication terminal (120) and the sensor transmitter (110) when information related to or associated with the sensor transmitter (110) or blood glucose information data is not stored at the communication terminal (120) by disconnecting the connection between the communication terminal (120) and the sensor transmitter (110) will be described.

In the present embodiment, the communication terminal (120) and the sensor transmitter (110) are communicationally connected (S201).

And, the communication terminal (120) transmit user information to the communicationally connected sensor transmitter (110) (S203).

The user information can be inputted into the communication terminal (120) by executing a program or application installed at the communication terminal (120) and performing a verification process regarding a user through a log-in process. The communication terminal (120) transmits the inputted user information to the sensor transmitter (110), and at that time, the transmitted user information may be a user ID, name, birthdate, and so on. And, the sensor transmitter (110) stores the user information received from the communication terminal (120).

The communication terminal (120) receives blood glucose information data from the communicationally connected sensor transmitter (110) (S205), stores the received blood glucose information data, and display it so that the user can check it.

And, after the communication connection between the communication terminal (120) and the sensor transmitter (110) is maintained, the communication connection between the communication terminal (120) and the sensor transmitter (110) is disconnected (S207).

As described above, the communication terminal (120) attempts the communication connection to the sensor transmitter (110) without a record that the sensor transmitter (110) is communicationally connected previously (S209).

Accordingly, the communication of the communication terminal (120) is reconnected with the sensor transmitter (110) (S211).

If the communication of the communication terminal (120) and the sensor transmitter (110) is reconnected like this, the sensor transmitter (110) transmits user information stored at the sensor transmitter (110) and various type information of the sensor transmitter (110) to the communication terminal (120) (S213).

At that time, the communication terminal (120) can request the sensor transmitter (110) for various type information, and in response to the request, the sensor transmitter (110) can transmit the information to the communication terminal (120).

The user information transmitted to the communication terminal (120) may be the user information which the communication terminal (120) transmitted to the sensor transmitter (110) at step 203. Additionally, the information of the sensor transmitter (110) may be identification or unique information of the sensor transmitter (110), such as an identifier and a serial number of the sensor transmitter (110), information on an activation time point of the sensor transmitter (110) and information on a usable time period of the sensor transmitter (110).

The communication terminal (120) determines whether the sensor transmitter (110) is a previously used sensor transmitter or not based on the information received from the sensor transmitter (110) (S215). The communication terminal (120) determines whether the reconnected sensor transmitter (110) is a previously used sensor transmitter or not based on the determination of whether user information exists in the information received from the sensor transmitter (110) at step 213. Accordingly, if the user information is included in the information received from the sensor transmitter (110), the communicationally connected sensor transmitter can be determined as a previously used sensor transmitter, and if the user information is not comprised in the information received from the sensor transmitter (110), the communicationally connected sensor transmitter can be determined as a sensor transmitter which has not been previously used.

If the communicationally connected sensor transmitter (110) is determined as a sensor transmitter which has not been previously used, the communication terminal (120) determines that the communicationally connected sensor transmitter (110) is new sensor transmitter, and therefore proceeds new connection.

However, if it is determined that the communicationally connected sensor transmitter (110) is a previously used sensor transmitter, whether a remaining usable time period of the communicationally connected sensor transmitter (110) is left is determined (S217).

The determination of whether the remaining usable time period of the communicationally connected sensor transmitter (110) is left is determined by calculating an actual user time period of the sensor transmitter (110) using time difference between an activation time point of the sensor transmitter (110) received from the sensor transmitter (110) at step S213 and a current time, and comparing the calculated actual use time period with the usable time period of the sensor transmitter (110) received from the sensor transmitter (110). Accordingly, if the calculated actual user time period is shorter than the usable time period received from the sensor transmitter (110), it is determined that the remaining usable time period of the sensor transmitter (110) is left, and, if the calculated actual user time period is equal to or longer than the usable time period received from the sensor transmitter (110), it is determined that the remaining usable time period of the communicationally connected sensor transmitter (110) is not left, and the communication terminal (120) terminates the communication connection with the sensor transmitter (110).

If it is determined that the communicationally connected sensor transmitter (110) is a previously used sensor transmitter and the remaining usable time period is left, the communication terminal (120) determines whether a user of the communicationally connected sensor transmitter (110) is the same as an existing user (S219).

At that step, the communication terminal (120) determines whether a user of the communicationally connected sensor transmitter (110) is the same as an existing user using determination of whether the user information received from the sensor transmitter (110) at step 213 and the user information verified by the communication terminal (120) match each other.

If it is determined that the user of the communicationally connected sensor transmitter (110) is different from an existing user, the communication terminal (120) terminates the communication connection with the sensor transmitter (110).

However, if it is determined that the user of the communicationally connected sensor transmitter (110) is the existing user, the communication terminal (120) requests a user to confirm whether to continue to use the sensor transmitter (110) (S221).

If a user command not to continue to use the communicationally connected sensor transmitter (110) is inputted, the communication terminal (120) terminates the communication connection with the sensor transmitter (110). However, if a user command to continue to use the communicationally connected sensor transmitter (110) is inputted, the communication terminal (120) receives blood glucose information data from the sensor transmitter (110) (S223).

The communication terminal (120) stores the blood glucose information data received from the sensor transmitter (110), and displays or outputs the received blood glucose information data on the communication terminal (120) so that the user can check it (S225).

At that time, because the previously stored blood glucose information data is not stored at the communication terminal (120), the communication terminal (120) can request the sensor transmitter (110) to transmit all blood glucose information data stored at the sensor transmitter (110), and the communication terminal (120) can display only the blood glucose information data received from the sensor transmitter (110) on the communication terminal (120) according to the present embodiment.

Here, the aa can store the measured blood glucose information data for about twelve (12) hours, and therefore the communication terminal (120) can receive from the sensor transmitter (110) and output or display the blood glucose information data of about twelve (12) hours.

And, if the usable time period of the sensor transmitter (110) is expired (S227), the communication terminal (120) terminates the communication connection with the sensor transmitter (110).

Figure 9:
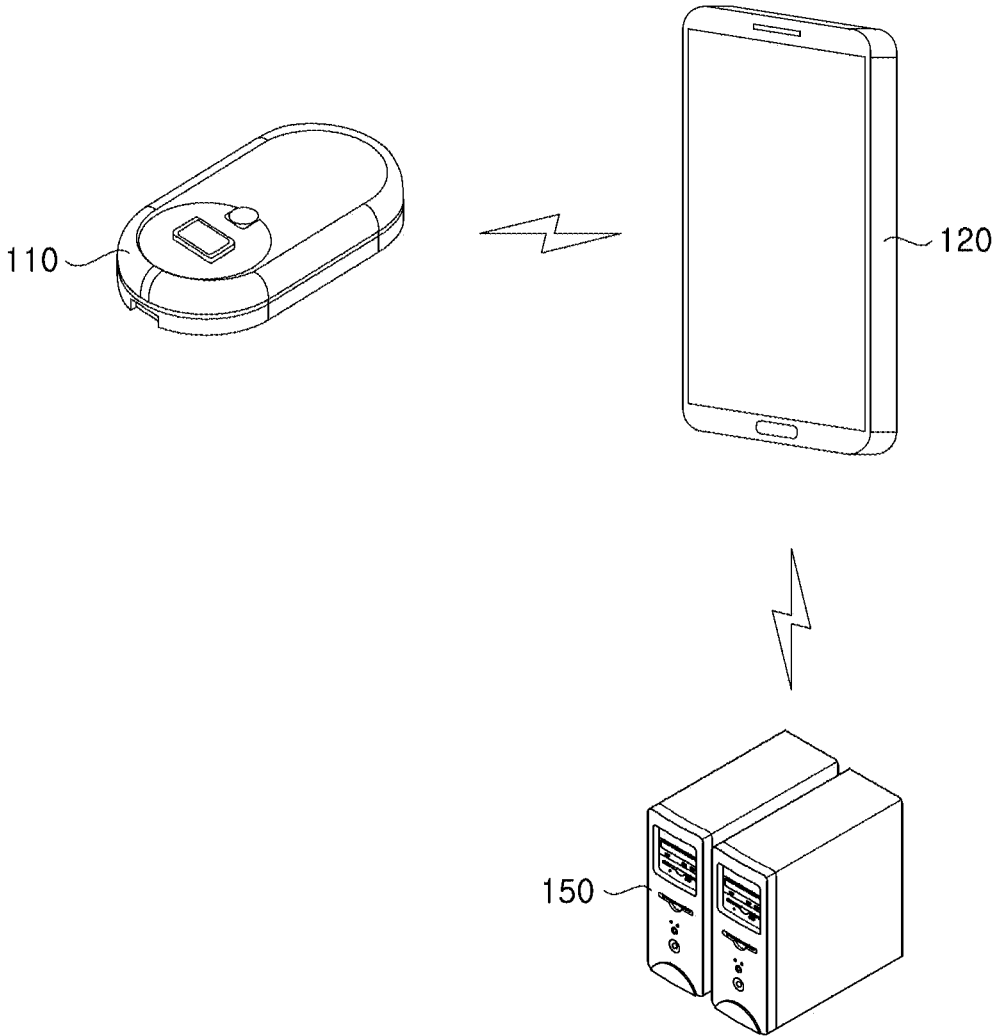
FIG. 9 is a schematic diagram for illustrating a continuous blood glucose monitoring system according to another embodiment of the present disclosure.

FIG. 9 is a schematic diagram for illustrating a continuous blood glucose monitoring system according to another embodiment of the present disclosure.

Still Another embodiment of a continuous blood glucose monitoring system (100) will be described. When describing the present embodiment, descriptions of the present embodiment of the present disclosure which are the same as or similar to those of other embodiments described above are omitted, and if necessary, the descriptions of the present embodiment may refer to FIGS. 1 to 7.

According to the present embodiment, the communication terminal (120) can communicate with the server (150). For this, the terminal communication unit (121) comprised in the communication terminal (120) can communicate with the server (150) through a mobile communication network or wifi communication network.

The communication terminal (120) receives information of the sensor transmitter (110) from the sensor transmitter (110), and transmits the received information of the sensor transmitter (110) and the user information to the server (150). The information of the sensor transmitter (110) may be identification or unique information of the sensor transmitter (110), such as an identifier and a serial number, information on a time point in which the sensor transmitter (110) is activated, and information on a usable time period of the sensor transmitter (110).

Additionally, the communication terminal (120) can receive the user information and the information of the sensor transmitter (110) from the server (150). The communication terminal (120) performs various kinds of determination on whether the sensor transmitter (110) of which communication is reconnected is to be used using the information received form the server (150). The various kinds of the determination may determine whether the reconnected sensor transmitter (110) is a previously used sensor transmitter, whether a remaining usable time period of the sensor transmitter (110) is left or whether a user who uses the sensor transmitter (110) is an existing user. And, the sensor transmitter (110) requests the user to confirm whether to continue to use the reconnected the sensor transmitter (110).

If the user confirms that the sensor transmitter (110) is to continue to be used, the communication terminal (120) receives from the sensor transmitter (110) and stores blood glucose information data and displays it so that the user can check it.

The server (150) can communicate with the communication terminal (120), and store the user information received from the communication terminal (120) and the information of the sensor transmitter (110). And, the server (150) can transmit the user information stored at the communication terminal (120) and the information of the sensor transmitter (110), and they can be transmitted in response to the request of the communication terminal (120).

Figure 10:
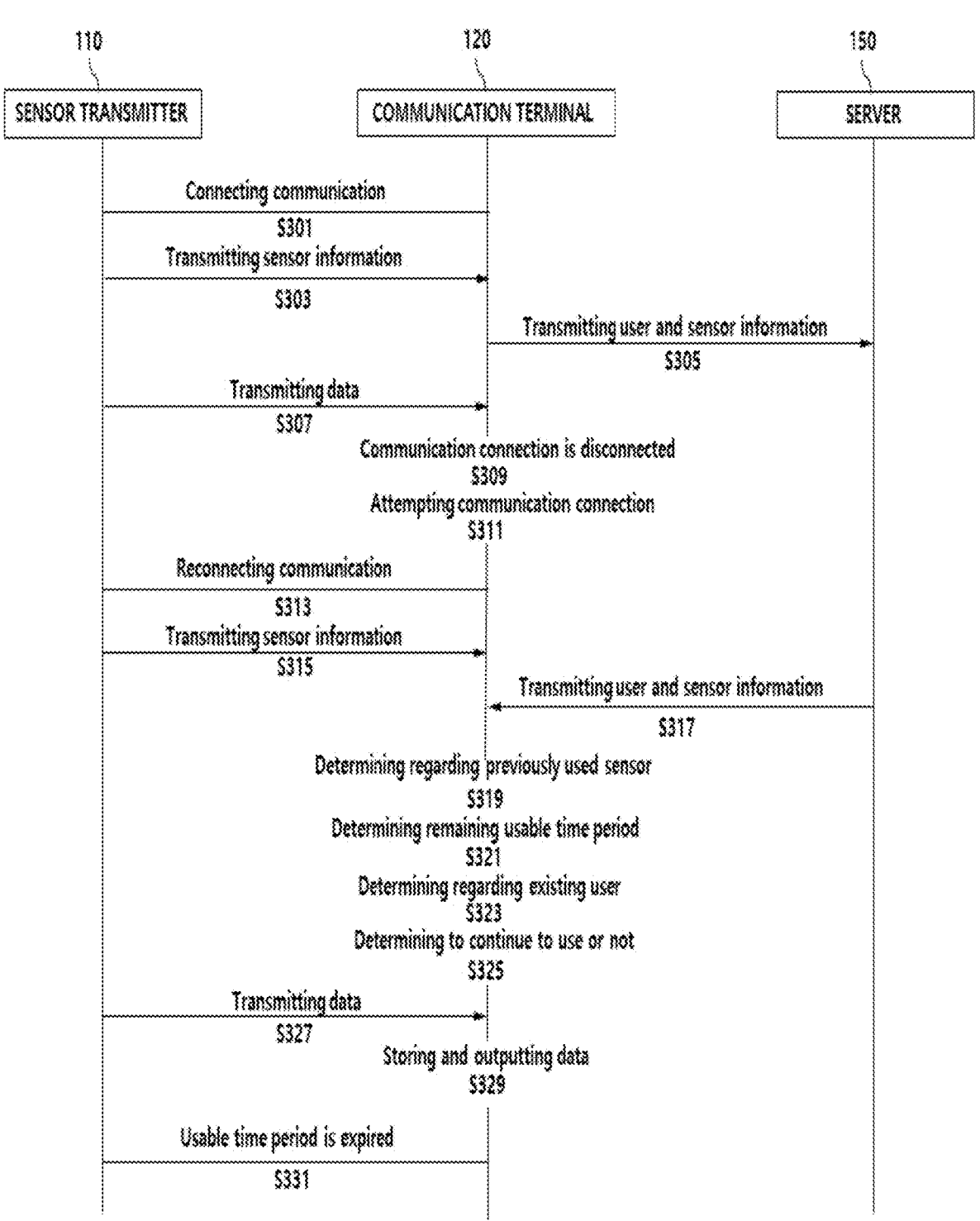
FIG. 10 is a flowchart for illustrating a method of communication connection of a continuous blood glucose monitoring system according to still another embodiment of the present disclosure.

FIG. 10 is a flowchart for illustrating a method of communication connection of a continuous blood glucose monitoring system according to still another embodiment of the present disclosure.

A method of communication connection of a continuous blood glucose monitoring system according to still another embodiment of the present disclosure will be described with reference to FIG. 10, and when describing the present embodiment, descriptions of the present embodiment of the present disclosure which are the same as or similar to those of other embodiments described above are omitted.

In the present embodiment, a case in which the communication of the communication terminal (120) and the sensor transmitter (110) is reconnected when the communication connection of the communication terminal (120) and the sensor transmitter (110) is disconnected will be described.

As described in other embodiments explained above, in a case that the communication connection between the communication terminal (120) and the sensor transmitter (110) is disconnected due to the uninstall or removal of the program or application from the communication terminal (120), information related to or associated with the sensor transmitter (110) or the previously received blood glucose information data may be deleted together. Or, the user can use a new communication terminal, and therefore the communication connection between the previously used communication terminal (120) and the sensor transmitter (110) may be disconnected. In those cases, information related to or associated with the previous sensor transmitter (110) or the blood glucose information data previously transmitted from the sensor transmitter (110) may not be stored at a new communication terminal (120).

Therefore, in the present embodiment, a case in which the communication of the communication terminal (120) and the sensor transmitter (110) is reconnected when no information related to or associated with the sensor transmitter (110) or no blood glucose information data is stored at the communication terminal (120) due to the disconnection of the communication connection of the communication terminal (120) and the sensor transmitter (110) will be described.

In the present embodiment, the communication of the communication terminal (120) and the sensor transmitter (110) is connected (S301).

If the communication terminal (120) and the sensor transmitter (110) are communicationally connected to each other, the communication terminal (120) receives information of the sensor transmitter (110) from the sensor transmitter (110) (S303).

Here, the received information of the sensor transmitter (110) may be information of the sensor transmitter (110), such as an identifier and a serial number of the sensor transmitter (110), information on a time point in which the sensor transmitter (110) is activated, and information on a usable time period of the sensor transmitter (110).

And, the communication terminal (120) transmits, to the server (150), the received information of the sensor transmitter (110) and the user information (S305).

The user information can be inputted into the communication terminal (120) by executing a program or application installed at the communication terminal (120) and performing a verification process regarding a user through a log-in process. The communication terminal (120) transmits the inputted user information to the server (150), and at that time, the transmitted user information may be a user ID, name, birthdate, and so on. And, the server (150) stores the user information received from the communication terminal (120) which are mapped to each other.

The communication terminal (120) receives blood glucose information data from the communicationally connected sensor transmitter (110) (S307), stores the received blood glucose information data, and displays or outputs it so that the user can check it.

And, the communication connection of the communication terminal (120) and the sensor transmitter (110) is disconnected (S309) after the communication connection of the communication terminal (120) and the sensor transmitter (110) is maintained.

As described above, the communication terminal (120) attempts the communication connection to the sensor transmitter (110) without a record that the sensor transmitter (110) is communicationally connected before (S311).

Accordingly, the communication of the communication terminal (120) is reconnected with the sensor transmitter (110) (S313).

If the communication of the communication terminal (120) and the sensor transmitter (110) is reconnected like this, the sensor transmitter (110) transmits various type information of the sensor transmitter (110) to the communication terminal (120) (S315).

The communication terminal (120) receives the user information and the information of the sensor transmitter (110) from the server (150) (S317). Here, the information received from the server (150) by the communication terminal (120) may be the information transmitted to the server (150) by the communication terminal (120) at step S305.

Accordingly, the communication terminal (120) performs various kinds of determination regarding the reconnected sensor transmitter (110) using the information received from the sensor transmitter (110) at step S315 and the information received from the server (150) at step S317.

The communication terminal (120) determines whether the reconnected sensor transmitter (110) is a previously used sensor transmitter (110) (S319).

The communication terminal (120) compares identification or unique information of the sensor transmitter (110) received from the sensor transmitter (110) with identification or unique information of the sensor transmitter (110) received from the server (150), and if the identification or unique information of the sensor transmitter (110) received from the sensor transmitter (110) matches, or is identical to, the identification or unique information of the sensor transmitter (110) received from the server (150), the communication terminal (120) determines that the reconnected sensor transmitter (110) is a previously used sensor transmitter. However, if the identification or unique information of the sensor transmitter (110) received from the sensor transmitter (110) does not match, or is not identical to, the identification or unique information of the sensor transmitter (110) received from the server (150), the communication terminal (120) determines that the reconnected sensor transmitter (110) is a new sensor transmitter, and proceeds new connection with the reconnected sensor transmitter (110).

When it is determined that the reconnected sensor transmitter (110) is a previously used sensor transmitter, the communication terminal (120) determines whether the remaining usable time period of the reconnected sensor transmitter (110) is left (S321).

at current time using information on an activation time point of the sensor transmitter (110) and an usable time period of the sensor transmitter (110), received from the sensor transmitter (110).

When the remaining usable time period of the sensor transmitter (110) is left, the terminal controller (127) maintains the communication connection of the sensor transmitter (110). However, if the remaining usable time period of the sensor transmitter (110) is not left, the terminal controller (127) terminates the communication connection with the sensor transmitter (110) to prevent the reuse of the sensor transmitter (110) of which remaining usable time period is expired.

The determination about whether the existing user of the reconnected sensor transmitter and the user match each other can be determined by determination of whether the user information acquired through the log-in process by the communication terminal (120) and the user information mapped to the sensor transmitter, received from the server (150), match or are identical to each other. However, if the user of the reconnected sensor transmitter (110) and the existing user are different from each other, the communication terminal (120) terminates the reconnected communication with the sensor transmitter (110).

When the user of the reconnected sensor transmitter (110) is the existing user, the communication terminal (120) outputs, to the user, a notification message asking whether to continue to use the sensor transmitter (110), and checks whether a user command to continue to use the reconnected sensor transmitter is inputted in response to the notification message (S325).

If a user command not to continue to use the sensor transmitter (110) is inputted, the communication terminal (120) terminates the communication connection with the sensor transmitter (110). However, if a user command to continue to use the sensor transmitter (110) is inputted, the communication terminal (120) receives blood glucose information data from the sensor transmitter (110) (S327).

At that time, the sensor transmitter (110) can transmit the blood glucose information data to the communication terminal (120) by the request from the communication terminal (120).

The communication terminal (120) stores the blood glucose information data received from the sensor transmitter (110), and outputs or displays the received blood glucose information data so that the user can check it (S329).

At that time, because the previously stored blood glucose information data is not stored at the communication terminal (120), the communication terminal (120) can display only the blood glucose information data received from the sensor transmitter (110) at step 327 on the communication terminal (120) according to the present embodiment.

If necessary, a step in which the communication terminal (120) transmits the blood glucose information data received from the sensor transmitter (110) at step 307 to the server (150) may be further comprised. At that time, the transmission of the blood glucose information data to the server (150) by the communication terminal (120) can be performed until the communication connection of the communication terminal (120) and the sensor transmitter (110) is disconnected at step S309.

Accordingly, when the communication terminal (120) receives data from the sensor transmitter (110) after the communication connection of the sensor transmitter (110) and the communication terminal (120) is reconnected, the communication terminal (120) can receive the blood glucose information data stored at the server (150). Accordingly, when storing and displaying or outputting the blood glucose information data at step S329, the blood glucose information data received from the server (150) also can be stored and displayed or outputted together.

And, if the usable time period of the sensor transmitter (110) is expired (S331), the communication terminal (120) terminates the communication connection with the sensor transmitter (110).

As described above, the foregoing detailed descriptions regarding the present disclosure have been presented by way of exemplary embodiments, but the detailed exemplary embodiments are presented as preferred examples, and therefore it should be understood that the present disclosure shall not be limited to those exemplary embodiments, and the scope of the present disclosure shall be defined by the Claims and all of their equivalents fall within the scope of the present disclosure.

What is claimed is:

1. A communication connection method, comprising:
receiving sensor transmitter information and user information from a sensor transmitter attachable to a body and configured to measure biometric information of the body, after connecting communication between the sensor transmitter and a communication terminal;
receiving information of a first sensor transmitter from a server; and
controlling communication connection based on the sensor transmitter information and the user information,
wherein the controlling of the communication connection comprises maintaining the communication connection, if the sensor transmitter is the first sensor transmitter, and
wherein the information of the first sensor transmitter received from the server comprises information about a time point at which the first sensor transmitter was activated and information about a usable time period of the first sensor transmitter.

2. The communication connection method of claim 1, wherein a record of the communication connection with the communication terminal is stored in the first sensor transmitter.

3. The communication connection method of claim 1, further comprising:
if the sensor transmitter is a second sensor transmitter newly connected to the communication terminal, storing information of the second sensor transmitter and a record of communication connection between the communication terminal and the second sensor transmitter.

4. The communication connection method of claim 1, further comprising:
before the controlling of the communication connection, comparing the information of the first sensor transmitter received from the server with the sensor transmitter information received from the sensor transmitter.

5. The communication connection method of claim 1, wherein, the controlling of the communication connection comprises maintaining the communication connection, if the sensor transmitter is the first sensor transmitter, a user of the sensor transmitter is a user of the first sensor transmitter, and a period of the first sensor transmitter is before expiration.

6. The communication connection method of claim 5, wherein the sensor transmitter information comprises information about a time point at which the sensor transmitter was activated and information about a usable time period of the sensor transmitter.

7. The communication connection method of claim 1, further comprising:
before the controlling of the communication connection, comparing the received user information with user information stored in the communication terminal.

8. The communication connection method of claim 1, further comprising:
before the controlling of the communication connection, comparing the user information received from the sensor transmitter with user information verified by the communication terminal.

9. The communication connection method of claim 1, wherein the controlling of the communication connection comprises maintaining the communication connection, if the sensor transmitter is the first sensor transmitter, a user of the sensor transmitter is a user of the first sensor transmitter, and input information for continued use of the first sensor transmitter is received from the user of the sensor transmitter.

10. The communication connection method of claim 1, further comprising:

receiving, by the communication terminal, biometric information data measured by the first sensor transmitter, and displaying the received biometric information data on the communication terminal, wherein the received biometric information data include biometric information data which has not been transmitted from the first sensor transmitter to the communication terminal for a time period of disconnection of the communication between the first sensor transmitter and the communication terminal.

* * * * *